(12) United States Patent
Kukita et al.

(10) Patent No.: US 9,791,412 B2
(45) Date of Patent: Oct. 17, 2017

(54) SENSING DEVICE

(71) Applicant: NIHON DEMPA KOGYO CO., LTD., Tokyo (JP)

(72) Inventors: Hiroyuki Kukita, Saitama (JP); Shunichi Wakamatsu, Saitama (JP); Wakako Shinobu, Saitama (JP)

(73) Assignee: NIHON DEMPA KOGYO CO., LTD., Tokyo (JP)

( * ) Notice: Subject to any disclaimer, the term of this patent is extended or adjusted under 35 U.S.C. 154(b) by 514 days.

(21) Appl. No.: 14/300,222

(22) Filed: Jun. 9, 2014

(65) Prior Publication Data

US 2014/0366611 A1 Dec. 18, 2014

(30) Foreign Application Priority Data

Jun. 12, 2013 (JP) .................................. 2013-123872

(51) Int. Cl.
*G01N 29/02* (2006.01)
*G01N 29/24* (2006.01)

(52) U.S. Cl.
CPC ....... *G01N 29/022* (2013.01); *G01N 29/2443* (2013.01)

(58) Field of Classification Search
CPC .......................... G01N 29/022; G01N 29/2443
See application file for complete search history.

(56) References Cited

U.S. PATENT DOCUMENTS

| 2010/0021346 A1* | 1/2010 | Wakamatsu | G01N 5/02 73/579 |
| 2010/0313636 A1* | 12/2010 | Wakamatsu | G01N 29/022 73/64.53 |
| 2012/0304776 A1* | 12/2012 | Novotny | G01N 29/022 73/668 |

FOREIGN PATENT DOCUMENTS

| JP | 2000-283905 | 10/2000 |
| JP | 2004-069661 | 3/2004 |
| JP | 2004-330008 | 11/2004 |
| JP | 2010-002413 | 1/2010 |
| JP | 2012-013535 | 1/2012 |
| JP | 2012-173274 | 9/2012 |
| JP | 2013-040892 | 2/2013 |

* cited by examiner

*Primary Examiner* — Laura Martin
*Assistant Examiner* — Alex Devito
(74) *Attorney, Agent, or Firm* — Jianq Chyun IP Office

(57) ABSTRACT

A sensing device is provided that has satisfactory sensing accuracy when a crystal unit where an excitation electrode is formed on both upper and lower surfaces of a piezoelectric piece is used to sense a sensing object. Adsorption regions are arranged in two places so as to intersect a direction of flow of a fluid, thus each of the adsorption regions senses the sensing object and reference regions are individually provided in these adsorption regions. A difference Δf1 between the oscillation frequencies of the regions and a difference Δf2 between the oscillation frequencies of the regions are added, and based on the result of the addition, whether the sensing object is present or not and its concentration are detected.

5 Claims, 13 Drawing Sheets (FRONT SURFACE SIDE)

SENSING DEVICE

CROSS REFERENCE TO RELATED APPLICATIONS

This application claims the priority benefit of Japanese application serial no. 2013-123872, filed on Jun. 12, 2013. The entirety of the above-mentioned patent application is hereby incorporated by reference herein and made a part of this specification.

TECHNICAL FIELD

This disclosure relates to a sensing device that makes an adsorption layer formed on an electrode provided on a piezoelectric piece adsorb a sensing object in a sample fluid and that senses the sensing object based on a variation in the natural vibration frequency of the piezoelectric piece.

DESCRIPTION OF THE RELATED ART

As a device that senses a trace substance contained in a fluid such as a solution or a gas, for example, a sensing device is known that utilizes, as a QCM (Quarts Crystal Microbalance), a crystal unit including a piezoelectric piece such as a crystal element and an excitation electrode formed on both upper and lower surfaces of the crystal element. Specifically, an adsorption layer that adsorbs a sensing object is formed on part of the excitation electrode, and based on a variation in the oscillation frequency of the crystal unit caused when the sensing object is adsorbed, whether the sensing object is present or not and its concentration are detected.

In such a QCM, a technology is known in which in order to enhance the accuracy of the sensing of the sensing object, a reference excitation electrode where the adsorption layer described above is not formed is separately formed on the crystal element, and exogenous noises (for example, a temperature, the viscosity of a fluid and a stress caused by the pressure of the fluid) around the QCM can be cancelled, that is, a so-called technology is known in which a configuration is achieved as a twin sensor.

As a technology for further enhancing the accuracy of the sensing of the sensing object, for example, a method of narrowing, as much as possible, the dimension (flow path height) of the height of a flow path of the fluid flowing through the upper side of the adsorption layer and a method of increasing the oscillation frequency of the crystal unit are known. However, in order to make the fluid flow through the adsorption layer, it is necessary to acquire the flow path height to some extent, and hence there is a limitation that the flow path height is narrowed whereas when the oscillation frequency of the crystal unit is increased, oscillation within a solution is more likely to become unstable.

Although patent documents 1 to 3 disclose a microchannel device, the twin sensor described above, a technology for providing four reaction electrodes and the like, the drawback described above is not examined.

[Patent document 1] JP2004-330008
[Patent document 2] JP2000-283905
[Patent document 3] JP2004-069661

SUMMARY

This disclosure is made in view of the foregoing conditions. Thus, a need exists for a sensing device which is not susceptible to the drawback mentioned above. When a crystal unit in which an excitation electrode is formed on both upper and lower surfaces of a piezoelectric piece is used to sense a sensing object, this sensing device has satisfactory accuracy of the sensing.

According to an aspect of this disclosure, there is provided a sensing device that passes, on one surface side of a piezoelectric piece, a fluid containing a sensing object from one side to the other side and that makes an adsorption layer on a surface of a common electrode formed on the one surface side of the piezoelectric piece adsorb the sensing object to sense the sensing object, the sensing device including: a first sensor portion that includes a first adsorption region in which the adsorption layer is formed on the surface of the common electrode, a first reference region which is provided in a direction intersecting a direction of flow of the fluid when seen from the first adsorption region and in which the surface is exposed without the adsorption layer being formed on the surface of the common electrode and first opposite electrodes which are individually formed on the other surface side of the piezoelectric piece so as to be opposite the first adsorption region and the first reference region, respectively; a second sensor portion that includes a second adsorption region in which the adsorption layer is formed on the surface of the common electrode in a position separate to the one side or the other side when seen from the first reference region, a second reference region which is provided in a direction intersecting the direction of flow of the fluid when seen from the second adsorption region and in which the surface is exposed without the adsorption layer being formed on the surface of the common electrode and second opposite electrodes which are individually formed on the other surface side of the piezoelectric piece so as to be opposite the second adsorption region and the second reference region, respectively; a flow path formation member for passing, on the one surface side of the piezoelectric piece, the fluid containing the sensing object from the one side to the other side; an oscillation circuit for oscillating the piezoelectric piece; a frequency measurement portion for measuring an oscillation frequency of the oscillation circuit; and a control portion that determines a first difference between an oscillation frequency of the piezoelectric piece between the first adsorption region and the first opposite electrode and an oscillation frequency of the piezoelectric piece between the first reference region and the first opposite electrode, and a second difference between an oscillation frequency of the piezoelectric piece between the second adsorption region and the second opposite electrode and an oscillation frequency of the piezoelectric piece between the second reference region and the second opposite electrode, so as to calculate a sum value of the first difference and the second difference.

The flow path formation member may include a first flow path along which the fluid passes through the first adsorption region and the second reference region, a second flow path along which the fluid passes through the first reference region and the second adsorption region, a fluid supply port which is formed in common in the first flow path and the second flow path and fluid discharge ports which are individually formed in end portions of the first flow path and the second flow path on the other side, and on a downstream side of the first flow path and the second flow path with respect to the fluid discharge ports, a switching portion for switching the first flow path and the second flow path may be provided.

Preferably, in the oscillation device of the present invention, the first adsorption region and the second reference region are provided so as to include a center portion of the first flow path in the direction intersecting the direction of the flow, and the first reference region and the second adsorption region are provided so as to include the center portion of the first flow path in the direction intersecting the direction of the flow, when a dimension of the first adsorption region in the direction intersecting the direction of the flow of the fluid is W1, a dimension of the second adsorption region in the direction intersecting the direction of the flow of the fluid is W2 and a width dimension of the flow path formed by the flow path formation member in the direction intersecting the direction of the flow of the fluid is L, (W1+W2)/L>0.5 and the oscillation circuit includes a first oscillation circuit that oscillates the first sensor portion and a second oscillation circuit that oscillates the second sensor portion.

Furthermore, preferably, in the oscillation device of the present invention, on an upstream side of the fluid suction port, a liquid pressing portion that switches inflow of the fluid from the fluid supply port and stop of the inflow of the fluid and a switch portion that switches a region of the piezoelectric piece connected to the oscillation circuit between the first sensor portion and the second sensor portion are provided. The control portion performs control so as to switch the switch portion between the first sensor portion and the second sensor portion when the inflow of the fluid from the fluid supply port is stopped, such that the oscillation frequency is measured. And, the control portion performs control so as to switch the switching portion between the first flow path and the second flow path, when the liquid pressing portion switches from the stop of the inflow of the fluid to the inflow of the fluid.

In this disclosure, when the adsorption layer formed on the common electrode of the piezoelectric piece is made to adsorb the sensing object in the fluid, the adsorption layers are formed in two places such that the adsorption layers are separate from each other in the direction intersecting the direction of flow of the fluid, and thus the sensing object is sensed by each of the adsorption layers. The reference region where the adsorption layer is not formed is individually formed in these adsorption layers, and the difference between the oscillation frequency of the piezoelectric piece and the oscillation frequency of the reference region when the sensing object is adsorbed is calculated for each of the adsorption layers. Then, these differences are added, and thus the results of the measurements of the sensing object in these adsorption layers are added. Hence, since the sensing object can be adsorbed over the direction intersecting the direction of flow of the fluid, it is possible to sense the sensing object highly accurately.

DETAILED DESCRIPTION

Figure 1:
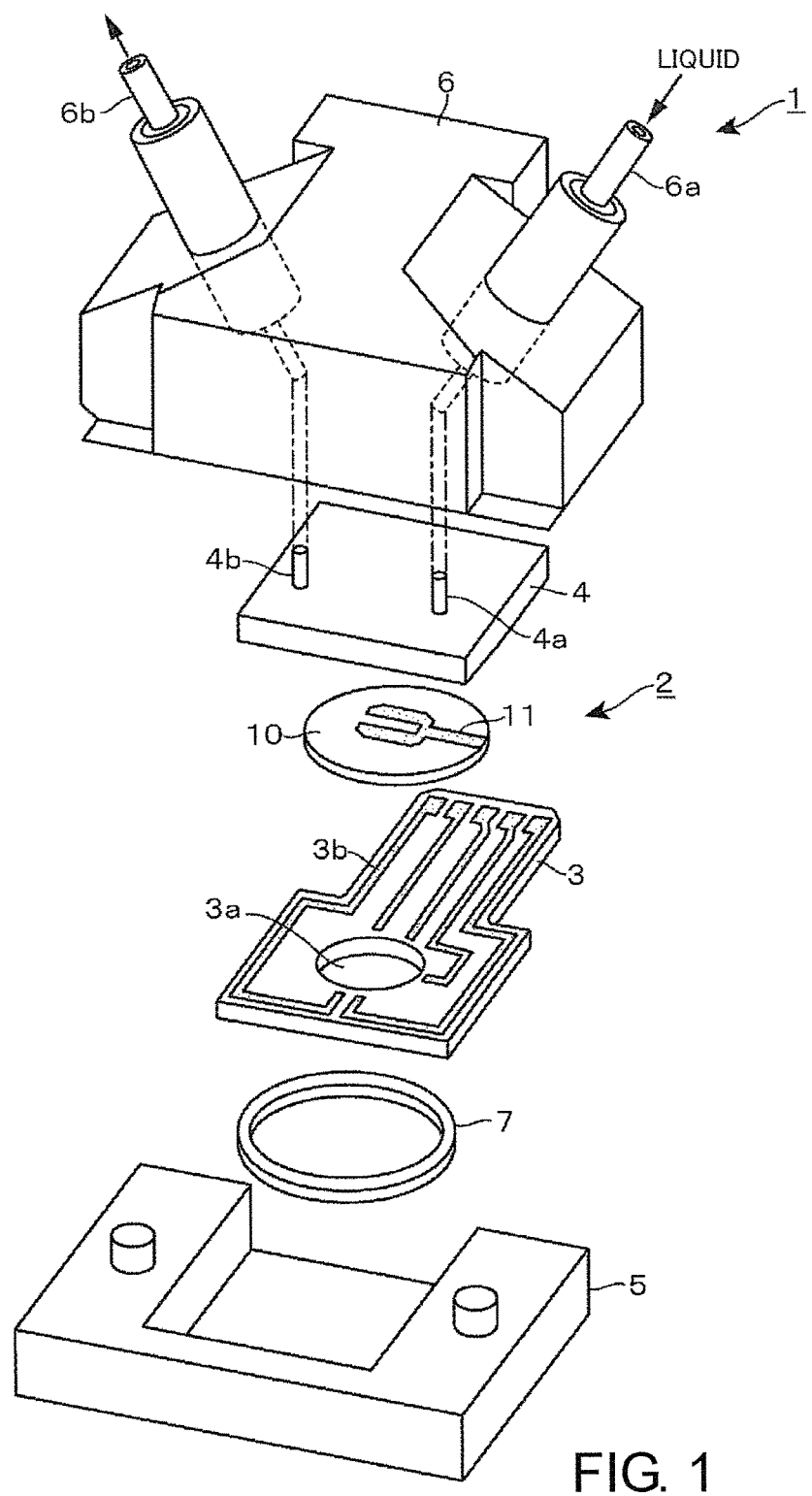
FIG. 1 is an exploded perspective view showing a sensor part of a sensing sensor disclosed here.

An example of an embodiment according to a sensing device disclosed here will be described with reference to FIGS. 1 to 10. A sensor part of this sensing device will first be described. A sensor unit 1 that is the sensor part includes: a crystal unit 2; a wiring substrate 3 that supports the crystal unit 2 from its back surface side and that is used for exchanging an electrical signal with the crystal unit 2; and a flow path formation member 4 for forming a flow path of a liquid on the upper surface side of the crystal unit 2. Reference numeral 5 in FIG. 1 represents a support member 5 that is arranged on the lower side of the wiring substrate 3, and reference numeral 6 represents a cover member 6 that is arranged on the upper side of the flow path formation member 4.

Figure 4:
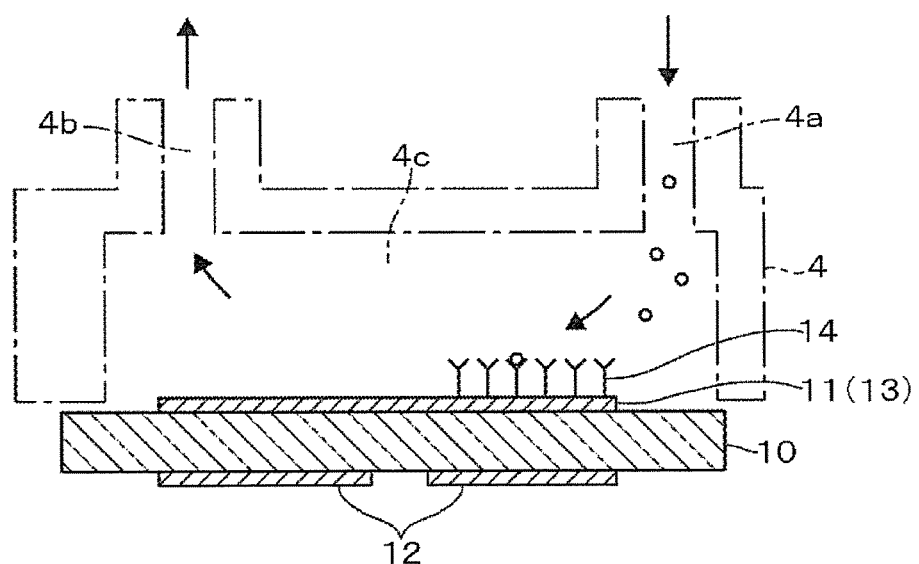
FIG. 4 is a vertical sectional drawing showing the crystal unit.

In the wiring substrate 3, an opening portion 3a is formed so as to avoid a region on the back surface side of the crystal unit 2 where excitation electrodes 12 to be described later are formed. On the lower side of the wiring substrate 3, a sealing member 7 whose upper side is opened and which is substantially cylindrical is arranged so as to hermetically block the region communicating with the back surface side of the crystal unit 2 through the opening portion 3a. The flow path formation member 4 described above is formed of, for example, rubber or resin, and includes a liquid supply tube 4a and a liquid discharge tube 4b for passing the liquid from one side (the right side in FIG. 1) to the other side (the left side in FIG. 1) in the surface of the crystal unit 2. In other words, as shown in FIG. 4, the flow path formation member 4 is formed substantially in the shape of a box whose center portion on the lower surface side is opened, and is configured to be hermetically in contact with the crystal unit 2 at its peripheral portion on the lower surface side. The liquid discharge tube 4a is connected to the one side on the upper surface side of the flow path formation member 4, and the liquid discharge tube 4b is connected to the other side on the upper surface side of the flow path formation member 4. Reference numerals 6a and 6b in FIG. 1 represent a liquid supply port 6a and a liquid discharge port 6b which are attached to the cover member 6 so as to communicate with the liquid supply tube 4a and the liquid discharge tube 4b, respectively.

Figure 2:
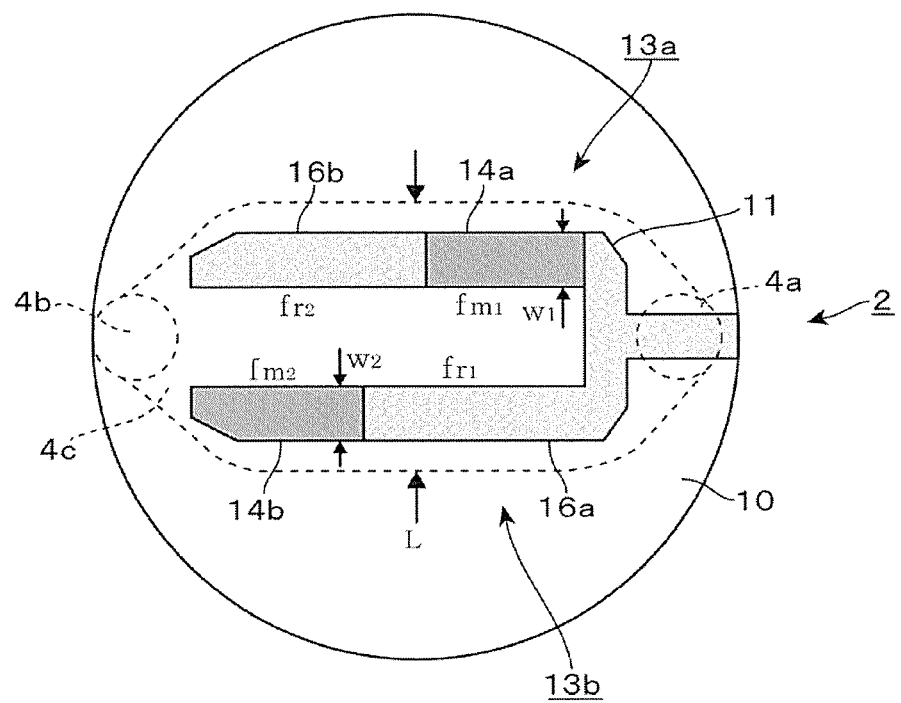
FIG. 2 is a plan view showing a crystal unit mounted on the sensor part.
Figure 3:
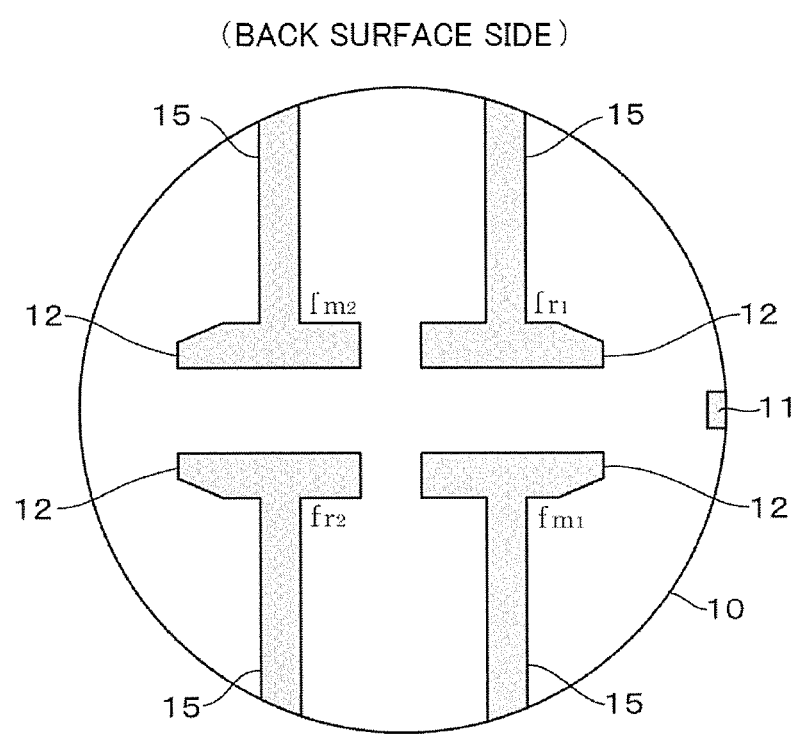
FIG. 3 is a plan view showing the crystal unit.

As shown in FIGS. 2 and 3, the crystal unit 2 includes: a crystal element 10 that is a piezoelectric piece which is formed substantially in the shape of a circular plate; a common electrode 11 that is formed on the upper surface side of the crystal element 10; and the above-described excitation electrodes 12 that are formed on the lower surface side of the crystal element 10. Here, the direction in which the liquid flows on the upper surface side of the crystal unit 2 (the direction extending from the liquid supply tube 4a to the liquid discharge tube 4b) is referred to as a front/rear direction. The common electrode 11 extends along the front/rear direction, and is formed substantially in the shape of a tuning fork. Specifically, the common electrode 11 is formed linearly at the base end portion of the lower side of the liquid supply tube 4a, and branches into two arm portions 13 and 13 halfway along a part extending toward the discharge side (the left side) of the liquid. Then, these arm portions 13 and 13 extend out toward the top end portion of the lower side of the liquid discharge tube 4b so as to be parallel to each other. As shown in FIG. 3, a part on the base end side of the common electrode 11 extends over the side surface side of the crystal element 10 and then extends out to the back surface side of the crystal element 10. In FIG. 2, the flow path (the opening portion in the center portion on the lower surface side of the flow path formation member 4) through which the liquid flows on the front surface side of the crystal unit 2 is indicated by broken lines.

With respect to these arm portions 13 and 13, symbols "13a" and "13b" are respectively attached to the arm portion 13 on the back side and the arm portion 13 on the front side in FIG. 2. Then, on the base end side (the right side) of the arm portion 13a on the back side, as shown in FIG. 4, an adsorption layer (reactive substance) 14 is formed that is made of an antibody or the like for adsorbing a sensing object such as an antigen. On the other hand, on the part on the top end side (the left side) of the arm portion 13a on the back side, the adsorption layer 14 is not provided, and the common electrode 11 is exposed. In the arm portion 13b on the front side, the adsorption layer 14 is formed on the top end side whereas on the base end side, the adsorption layer 14 is not formed, and the common electrode 11 is exposed. In FIG. 4, the flow path formation member 4 is shown in a simplified manner by dashed lines.

Here, the part where the adsorption layer 14 is formed in the arm portion 13a on the back side is referred to as a "first adsorption region 14a", and the part where the adsorption layer 14 is formed in the arm portion 13b on the front side is referred to as a "second adsorption region 14b". The region where the adsorption layer 14 is not formed in the arm portion 13b on the front side (the region opposite the first adsorption region 14a) forms a first reference region 16a for the first adsorption region 14a. In other words, as will be described in detail later, when a sample solution containing the sensing object is supplied from the liquid supply tube 4a to the surface of the crystal unit 2, the sensing object is adsorbed to the first adsorption region 14a, and in the crystal element 10 on the lower side of the first adsorption region 14a, its oscillation frequency is lowered based on the adsorption of the sensing object. On the other hand, since in the crystal element 10 on the lower side of the first reference region 16a, its oscillation frequency is not lowered, whether the sensing object is present or not and its concentration are detected based on the difference between these oscillation frequencies. The first adsorption region 14a and the first reference region 16a form a first sensor portion.

The region where the adsorption layer 14 is not formed in the arm portion 13a on the back side likewise forms a second reference region 16b for the second adsorption region 14b. Hence, when seen from the first adsorption region 14a, the first reference region 16a and the second adsorption region 14b each are provided in a direction intersecting the direction in which the liquid flows. In other words, when seen from the first adsorption region 14a, the first reference region 16a is arranged in the direction intersecting the direction of the flow. Moreover, when seen from the first adsorption region 14a, the second adsorption region 14b is arranged in a position intersecting the direction of the flow and separate to the downstream side (the other side) in the direction of the flow. The second adsorption region 14b and the second reference region 16b form a second sensor portion.

Here, as shown in FIG. 2, the width dimension (the width dimension of the opening portion in the lower surface of the flow path formation member 4) of the flow path of the liquid in the direction intersecting the direction of the flow of the liquid on the surface of the crystal unit 2 when seen in plan view is referred to as "L", and the total dimension of the width dimensions W1 and W2 of the adsorption regions 14a and 14b in the intersecting direction described above is assumed to be "W (W=W1+W2)". A proportion R (R=W/L) of the dimension W in the width dimension L is preferably maximized (close to 1) such that as will be described later, the sensing object contained in the sample solution is adsorbed as much as possible. In this example, the proportion is set at 0.5 to 0.7.

The excitation electrodes 12 on the back surface side of the crystal element 10 are arranged independently of each other opposite the above-described regions 14a, 14b, 16a and 16b, respectively, and are individually connected to drawing electrodes 15, respectively that extend out to the peripheral portion of the crystal element 10 on the back surface side of the crystal element 10. Specifically, on the back surface side of the crystal element 10, the first excitation electrodes 12 and 12 are formed at two places so as to be opposite the first adsorption region 14a and the first reference region 16a, respectively and to be separate from each other in the direction intersecting the direction of the flow of the liquid. Moreover, the second excitation electrodes 12 and 12 are arranged at two places so as to be opposite the second adsorption region 14b and the second reference region 16b, respectively and to be separate from each other in the direction intersecting the direction of the flow of the liquid.

These drawing electrodes 15 and the end portion of the common electrode 11 extending out to the back surface side of the crystal element 10 are, as shown in FIG. 1, connected to an oscillation circuit 32 to be described later through a conductive path 3b formed on the surface of the wiring substrate 3. Hence, the regions 14a, 14b, 16a and 16b are configured such that the regions can oscillate independently of each other between the regions and the excitation electrodes 12, which are opposite the regions through the crystal element 10.

When, the sensing object is adsorbed to the adsorption layers 14 on the adsorption regions 14a and 14b in this way, as described previously, the oscillation frequency on the side of the regions 14a and 14b is lowered whereas on the side of the reference regions 16a and 16b, the lowering of the oscillation frequencies based on the adsorption of the sensing object does not occur. Hence, the difference Δf1 (Δf2)

between the oscillation frequency fm1 (fm2) on the side of the adsorption region 14a (14b) and the oscillation frequency fr1 (fr2) on the side of the reference region 16a (16b) is calculated, and thus whether the sensing object is present in the sample solution or not and its concentration are detected. In this disclosure, as will be described later, these differences $\Delta f1$ and $\Delta f2$ are added, and thus the sensing object is detected highly accurately. In FIGS. 2 and 3, the frequencies are also shown so that the correlation of the regions 14a, 14b, 16a and 16b between the common electrode 11 and the excitation electrode 12 is indicated.

Figure 5:
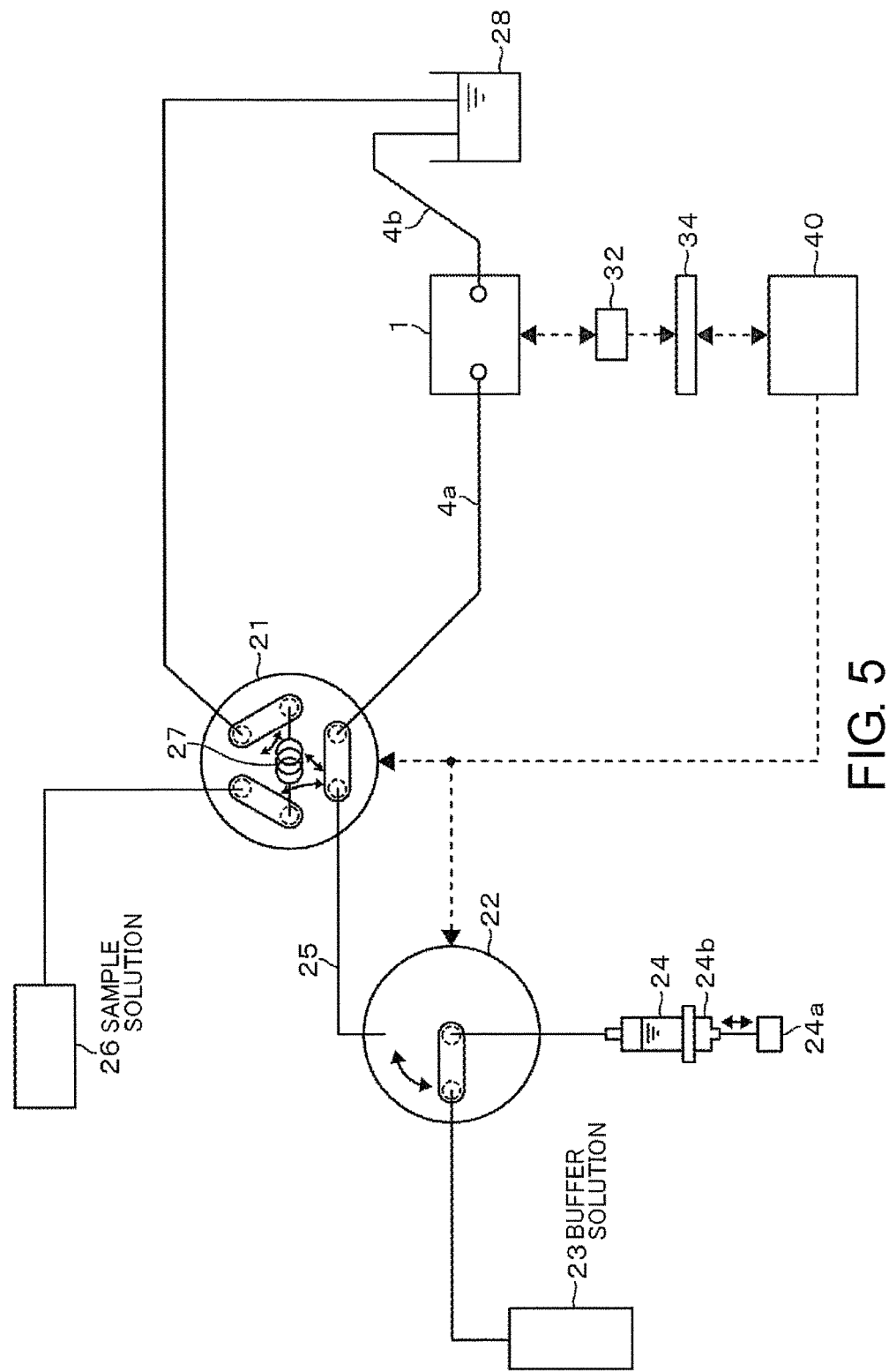
FIG. 5 is a schematic view showing the overall configuration of the sensing device.
Figure 6:
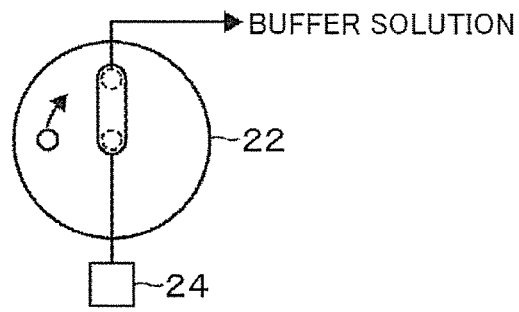
FIG. 6 is a schematic view showing how a liquid is passed in the sensing device.
Figure 7:
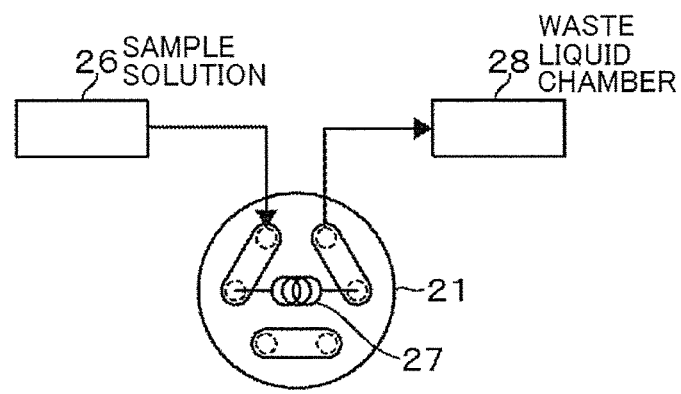
FIG. 7 is a schematic view showing how the liquid is passed in the sensing device.

Then, the configuration of the portions other than the sensor unit 1 in the sensing device will be described below. As shown in FIG. 5, on the upstream side of the liquid supply tube 4a, a liquid switching valve 21 formed with a six-way valve or the like and a buffer solution drawing valve 22 are arranged in this order from the side of the sensor unit 1. A storage portion 23 in which a buffer solution (for example, a phosphate buffer solution) is stored and a buffer solution holding portion 24 such as a syringe pump are connected to the buffer solution drawing valve 22. The flow path of the liquid in the buffer solution drawing valve 22 is arranged as shown in FIG. 5, the buffer solution is drawn from the storage portion 23 through the valve 22 to the buffer solution holding portion 24, then the flow path of the buffer solution drawing valve 22 is switched as shown in FIG. 6, and thus the buffer solution is pushed out to the side of the sensor unit 1 by the buffer solution holding portion 24. Reference numeral 24a in FIG. 5 represents a drive portion 24a for moving forward or backward a liquid pressing portion 24b such as a syringe that is provided in the buffer solution holding portion 24 in order to push the buffer solution stored in the buffer solution holding portion 24 out to the side of the sensor unit 1 or to draw the buffer solution in the storage portion 23 to the buffer solution holding portion 24, and the drive portion 24a is configured such that the speed at which the liquid pressing portion 24b is moved forward or backward can be freely adjusted. In FIG. 6, the configuration of the buffer solution holding portion 24 is shown in a simplified manner.

Figure 8:
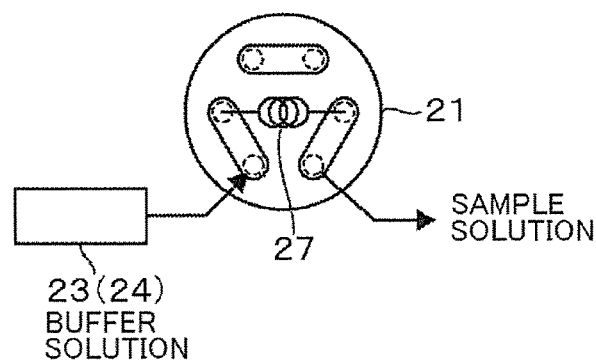
FIG. 8 is a schematic view showing how the liquid is passed in the sensing device.

A liquid supply path 25 extending from the buffer solution drawing valve 22 and a sample solution storage portion 26 in which the sample solution such as blood or serum is stored are connected to the liquid switching valve 21. In this liquid switching valve 21, the sample solution is temporarily stored (see FIG. 7) in a column 27 that forms a liquid storage portion provided within the liquid switching valve 21, then the flow path of the valve 21 is switched as shown in FIG. 8 and thus the sample solution in the column 27 is pushed out to the side of the sensor unit 1 by the sample solution of the buffer solution holding portion 24. Hence, the sample solution corresponding to the volume of the column 27 is supplied to the side of the sensor unit 1. Reference numeral 28 in FIG. 5 represents a waste liquid portion 28 that is provided in common to the downstream side of the liquid discharge tube 4b in the sensor unit 1 and the downstream side of the column 27 in the liquid switching valve 21.

Figure 9:
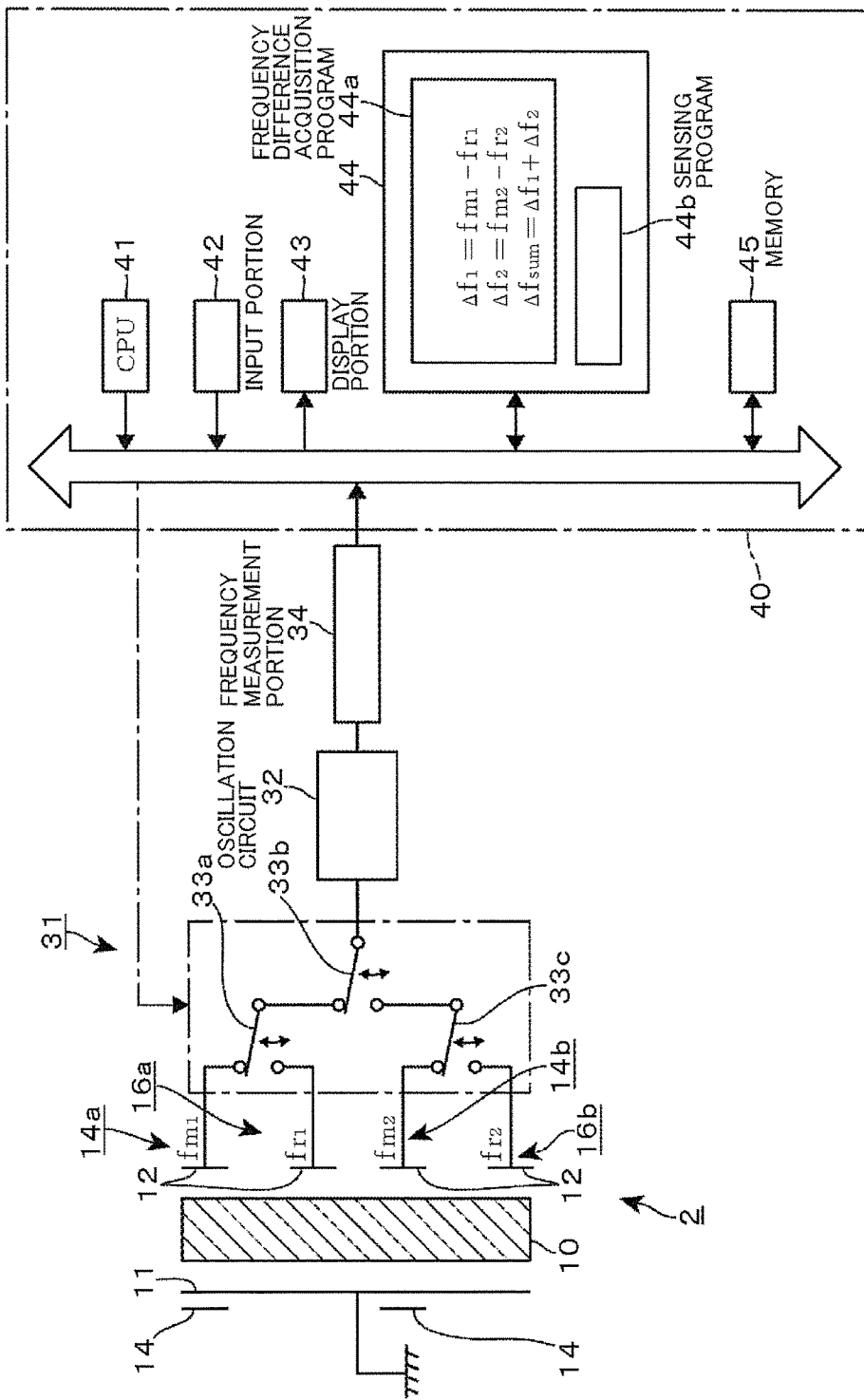
FIG. 9 is a simplified schematic view showing, in a simplified manner, the sensing device and a control portion arranged in the sensing device.
Figure 10:
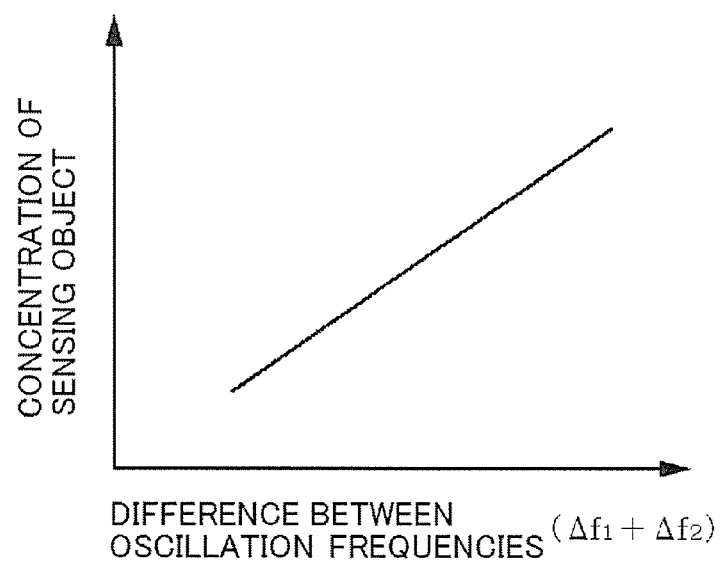
FIG. 10 is a schematic view showing an example of a correlation between a frequency measured by the sensing device and the concentration of a sensing object.

As shown in FIGS. 5 and 9, the oscillation circuit 32 is connected to the crystal unit 2 through the conductive path 3b formed on the surface of the wiring substrate 3 described above and a switch portion 31. This switch portion 31 oscillates any one of the regions 14a, 14b, 16a and 16b described previously (specifically, the crystal element 10 between the individual regions and the excitation electrodes 12), and takes in an oscillation output (frequency signal) in the one region mentioned above to the side of the oscillation circuit 32. Specifically, as shown in FIG. 9, the switch portion 31 is formed with three switches 33a to 33c. Between the regions 14a and 16a and the oscillation circuit 32, the first switch 33a and the second switch 33b are arranged in this order from the side of the crystal unit 2, and the first switch 33a is configured so as to connect the oscillation circuit 32 to any one of the regions 14a and 16a. The second switch 33b is arranged so as to be freely switched between a connection point on the side of the regions 14a and 16a and the connection portion on the side of the regions 14b and 16b. Between the regions 14b and 16b and the second switch 33b, the third switch 33c is arranged that is configured so as to connect any one of the regions 14b and 16b to the oscillation circuit 32. In FIG. 5, the switch portion 31 is omitted.

On the side of the subsequent stage of the oscillation circuit 32, a frequency measurement portion 34 for measuring the oscillation frequency in the oscillation circuit 32 is provided, and a control portion 40 is connected to the frequency measurement portion 34. The control portion 40 includes a CPU 41, an input portion 42 that is formed with, for example, a button for starting the measurement of the sensing object by an operator and the like, a display portion 43 that displays the result of the measurement and a program 44 for measuring the sensing object.

The program 44 includes a frequency difference acquisition program 44a in which as described previously, the difference $\Delta f1$ ($\Delta f1=fm1-fr1$) between the oscillation frequencies of the regions 14a and 16a and the difference $\Delta f2$ ($\Delta f2=fm2-fr2$) between the oscillation frequencies of the regions 14b and 16b are individually calculated, and in which the total value $\Delta fsum$ ($\Delta fsum=\Delta f1+\Delta f2$) of these differences $\Delta f1$ and $\Delta f2$ is calculated. The program 44 also includes a sensing program 44b in which the sensing object is determined based on the result (the total value $\Delta fsum$) of the calculation obtained by the frequency difference acquisition program 44a and data (see, for example, FIG. 10) on which a correlation between the calculation result and the concentration of the sensing object is previously determined. In other words, the sensing program 44b has the function of checking the calculation result against a calibration curve (the data), for example, comparing the calculation result with a threshold value to determine whether the sensing object is present or not or reading, from the calibration curve, the concentration corresponding to the calculation result to display the concentration of the sensing object. Reference numeral 45 in FIG. 9 represents a memory 45, and the memory 45 is configured such that in the process of sequentially measuring chronological data at the frequencies of the regions 14a, 14b, 16a and 16b while the switch portion 31 is performing switching at a high speed, until the calculation is completed by the frequency difference acquisition program 44a described above, the chronological data described above is stored. In FIG. 9, the crystal unit 2 is shown in a simplified manner.

Figure 11:
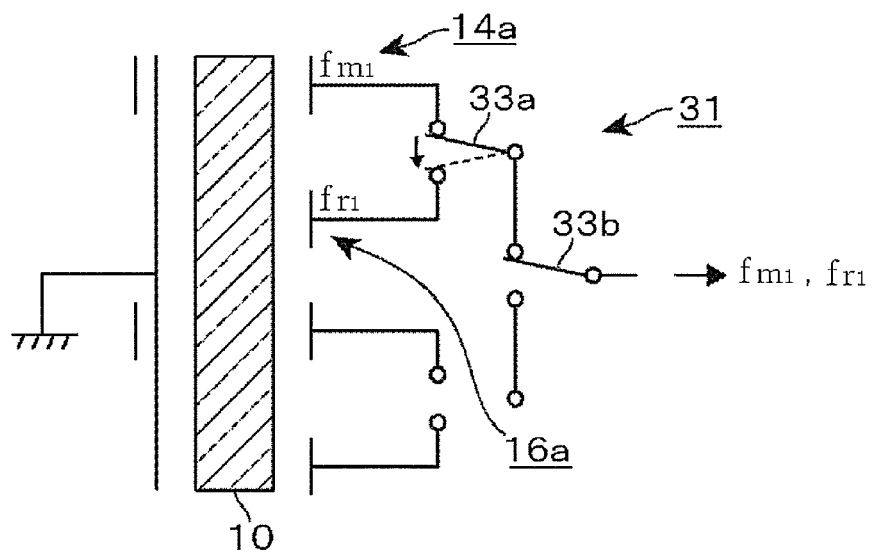
FIG. 11 is a schematic view showing how an oscillation frequency is switched by the sensing device.

Then, the action of the sensing device described above will be described with reference to FIGS. 11 to 13. First, for example, as shown in FIG. 11, the switch portion 31 is set on the side of the first adsorption region 14a, and the oscillation frequency fm1 in the adsorption region 14a is measured. Then, as indicated by a broken line, the switch portion 31 is switched to the side of the first reference region 16a, and the oscillation frequency fr1 in this reference region 16a is measured. Although the difference $\Delta f1$ between these oscillation frequencies fm1 and fr1 is calculated by the program 44a described previously, since the supply of the sample solution is not started at this time, the difference $\Delta 1$ is zero.

Figure 12:
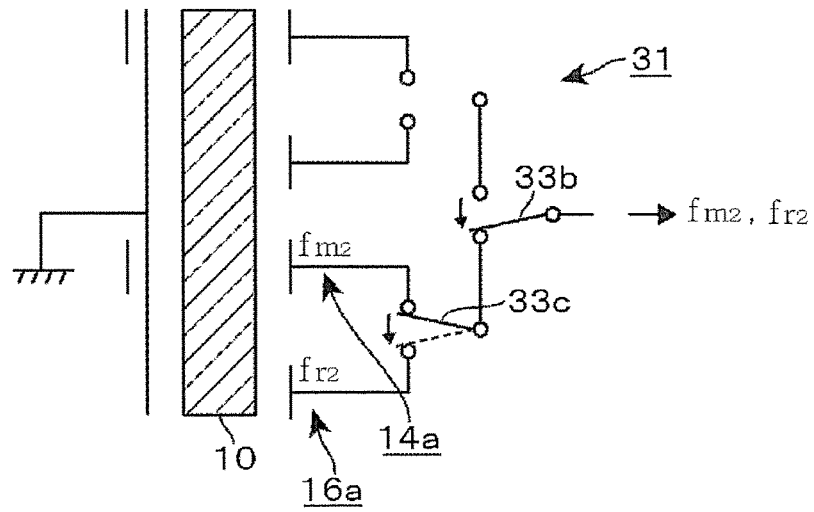
FIG. 12 is a schematic view showing how the oscillation frequency is switched by the sensing device.

Then, as shown in FIG. 12, the switch portion 31 is switched to the side of the second adsorption region 14*b*, and the oscillation frequency fm2 in this second adsorption region 14*b* is measured. Then, likewise, the switch portion 31 is switched to the side of the second reference region 16*b*, and the oscillation frequency fr2 in the second reference region 16*b* is measured. The difference Δf2 between these oscillation frequencies fm2 and fr2 is likewise zero before the start of the sample solution. Hence, the sum value Δfsum of these differences Δf1 and f2 is zero.

While as described above, the switch portion 31 is being switched at a period of, for example, about 250 msec., the buffer solution in the storage portion 23 is drawn to the buffer solution holding portion 24, and the buffer solution is pushed out to the surface of the crystal unit 2 through the liquid supply tube 4*a*. When the buffer solution makes contact with the surface of the crystal unit 2, the crystal unit 2 becomes difficult to oscillate due to the viscosity and the stress of the buffer solution, and thus the oscillation frequencies fm1, fr1, fm2 and fr2 are individually lowered.

Then, after the supply of the buffer solution is continued while the switch portion 31 is being switched until these oscillation frequencies fm1, fr1, fm2 and fr2 reach certain values, the supply of the sample solution to the crystal unit 2 is started. Specifically, as described above with reference to FIG. 8, the flow path within the liquid switching valve 21 is switched to the side of the column 27, and the sample solution within the column 27 is pushed out to the side of the sensor unit 1 by the buffer solution of the buffer solution holding portion 24.

When the sample solution reaches the lower end portion of the liquid supply tube 4*a*, the sample solution is diffused over the regions where the arm portions 13*a* and 13*b* are formed, and is passed to the liquid discharge tube 4*b*. Then, when the sensing object contained in the sample solution makes contact with the adsorption regions 14*a* and 14*b*, the sensing object is adsorbed to the adsorption layer 14 in the adsorption regions 14*a* and 14*b*, and the oscillation frequencies fm1 and fm2 on the side of the absorbing regions 14*a* and 14*b* are lowered. On the other hand, since in the reference regions 16*a* and 16*b*, the sensing object is not absorbed, the oscillation frequencies fr1 and fr2 are not lowered. Hence, as already described in detail, the differences Δf1 and f2 and the sum value Δfsum of these differences Δf1 and f2 are calculated, and whether the sensing object is present or not and its concentration are detected based on the calibration curve.

Here, a case where the concentration of the sensing object contained in the sample solution is low will be examined. Specifically, for example, when the sample solution is passed along the direction of the length of the first adsorption region 14*a* from the upstream side (the side of the liquid supply tube 4*a*) to the downstream side (the side of the liquid discharge tube 4*b*), it is assumed that the adsorption of the sensing object has already been completed on the upstream side, thus the sensing object is depleted at the downstream end of the first adsorption region 14*a* and the sensing object is not adsorbed to the adsorption layer 14 at the downstream end. In such a case, the sensing of the sensing object does not contribute to the part of the first adsorption region 14*a* on the downstream side with respect to the position in which the adsorption of the sensing object is completed, and thus in other words, it can be said that it is a useless region. On the other hand, the sensing object flowing through a position apart in a direction intersecting the direction of the flow of the liquid as seen from the first adsorption region 14*a* is not adsorbed to the first adsorption region 14*a*. Hence, in terms of requirement for capturing (adsorbing) the sensing object contained in the sample solution as much as possible, that is, in order for the accuracy of the sensing of the sensing object in the sensing device to be enhanced, the sensing object flowing through a region apart from the first adsorption region 14*a* is preferably also adsorbed to the adsorption layer 14.

Figure 13:
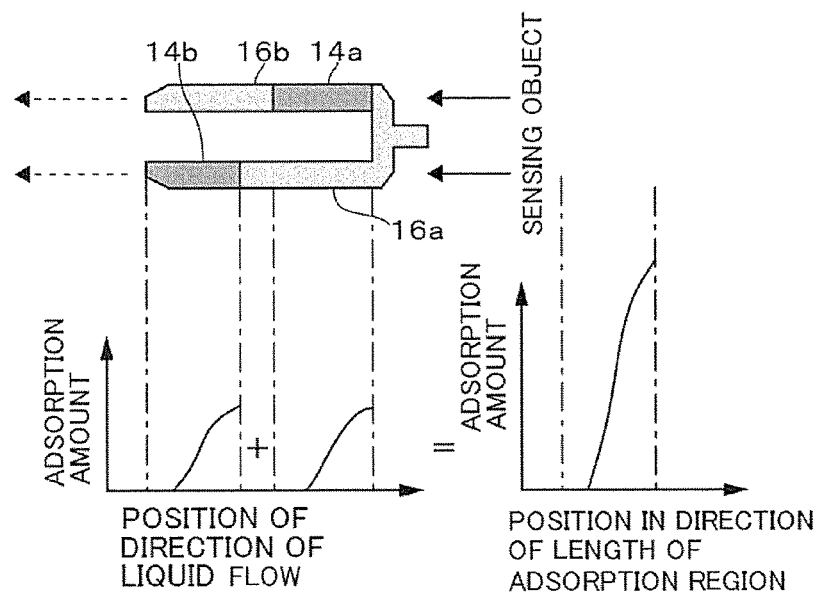
FIG. 13 is a schematic view showing an example of the result of sensing obtained by the sensing device.

Hence, in this disclosure, in a direction intersecting the direction of the flow of the liquid as seen from the first adsorption region 14*a*, the second adsorption region 14*b* separate from the first adsorption region 14*a* is provided, and the reference regions 16*a* and 16*b* are individually provided in theses adsorption regions 14*a* and 14*b*. Then, the results (Δf1 and Δf2) of the detection of the sensing object in the regions 14*a* and 14*b* are added. In other words, these adsorption regions 14*a* and 14*b* are aligned to intersect the direction of the flow of the liquid such that a smaller amount of sensing object is adsorbed to the adsorption layer 14 and is discharged. Hence even if as shown in FIG. 13, the concentration of the sensing object contained in the sample solution is low, it is possible to detect the sensing object highly accurately.

Figure 14:
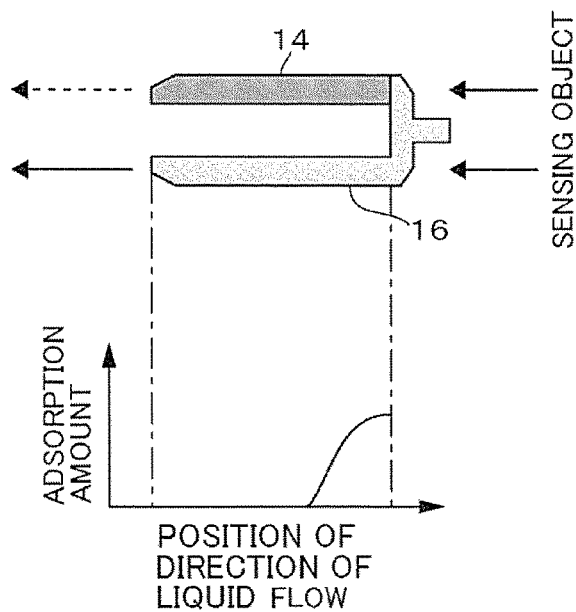
FIG. 14 is a schematic view showing an example of the result of sensing obtained by a conventional sensing device.

In other words, in a conventional example (an example where only one pair of the adsorption layer 14 and the reference region 16 is formed), as shown in FIG. 14, when a dilute solution is used as the sensing object, the adsorption of the sensing object does not naturally occur in the direction of the length of the adsorption layer 14 on the downstream side with respect to the position in which the adsorption of the sensing object is completed, and thus the accuracy of the sensing is only slightly high. Since the adsorption of the sensing object does not occur in the part where the reference region 16 is arranged, it can be said that the sensing object flowing through such a part is discharged wastefully. On the other hand, in this disclosure, the adsorption regions 14*a* and 14*b* are provided in two places, and the results of the detection in these adsorption regions 14*a* and 14*b* are added. Hence, the accuracy of the sensing of the sensing object is about twice as high as that in the conventional example.

Specifically, when the downstream side is seen from the upstream side in the direction of the flow of the liquid, in this disclosure (FIG. 13), the areas where the adsorption layer 14 is formed is twice as large as that in the conventional example (FIG. 14). Although in this disclosure, the length dimension of the adsorption layer 14 is about half as long as that in the conventional example, it is found, from a widely known serve ray formula (mathematical expression for determining the amount of sensing object adsorbed from the area of the electrode and a variation in frequency before and after the adsorption), that the sensitivity of the adsorption layer 14 per unit area in this disclosure is about the same as in the conventional example. In other words, since for the measurement of the dilute concentration to such a degree that the adsorption is not saturated, in this disclosure, the amount of adsorption layer 14 is doubled, the two measurement results (Δf1 and Δf2) are determined and these measurement results are added, it is possible to obtain the amount of adsorption about twice as much as in the conventional example.

In the embodiment described above, the two adsorption regions 14*a* and 14*b* are arranged in two places so as to intersect the direction of the flow of the liquid, the sensing object is sensed by each of the adsorption regions 14*a* and 14*b* and the reference regions 16*a* and 16*b* are individually provided in these adsorption regions 14*a* and 14*b*. The difference Δf1 between the oscillation frequencies in the regions 14*a* and 16*a* and the difference Δf2 between the oscillation frequencies in the regions 14b and 16b are added. Hence, since it is possible to adsorb the sensing object over the direction in which to intersect the direction of the flow of the liquid, it is possible to sense the sensing object highly accurately while reducing the effects of external disturbances (the temperature, the viscosity of the sample solution and the stress of the sample solution).

Figure 15:
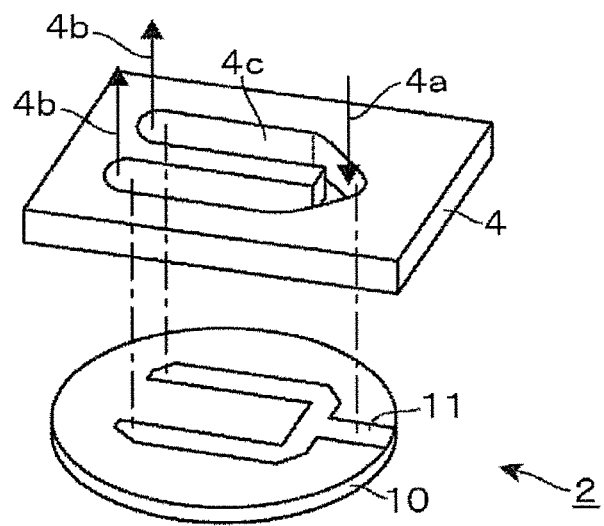
FIG. 15 is an exploded perspective view showing another example of the sensing device.

Then, another example of this disclosure will be described with reference to FIGS. 15 to 18. In this example, with respect to the parts of the flow path formation member 4 and the crystal unit 2 on the downstream side are configured such that the sensing object contained in the sample solution is adsorbed to the adsorption layer 14 as much as possible. Specifically, as shown in FIG. 15, a flow path 4c through which the liquid flows is branched into two flow paths according to (along) the arm portions 13a and 13b in the common electrode 11. FIG. 15 shows a state of the flow path formation member 4 where the flow path formation member 4 is cut in the horizontal direction in an arbitrary position in the direction of the height of the flow path formation member 4.

Specifically, as described previously, the flow path 4c is formed in common in these arm portions 13a and 13b, and thus in the distribution of the flow speed of the liquid, the speed is the highest in the center portion (part between the arm portions 13a and 13b) in the direction perpendicular to the direction of the flow of the liquid and the speed is decreased toward the end portion from the center portion. Hence, in the regions on the upper side of the arm portions 13a and 13b, the flow speed of the liquid is not significantly high. Thus, the sensing object contained in the sample solution flows through the region where the adsorption layer 14 is not formed, between the arm portions 13a and 13b.

Figure 16:
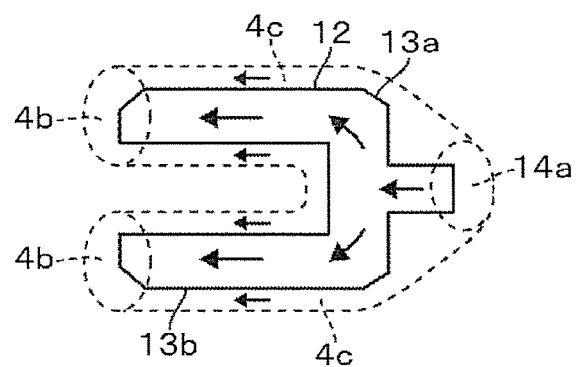
FIG. 16 is a plan view showing a part of the sensing device in the another example.

Hence, in this example, in the arm portions 13a and 13b, the dedicated flow paths 4c are respectively formed, and as shown in FIG. 16, the liquid is made to flow through the center portion of each of the arm portions 13a and 13b as much as possible. In other words, in the example described above, in the part through which the liquid flows the fastest, a wall surface portion of the flow path formation member 4 is formed such that the flow path 4c of the arm portions 13a and 13b is branched into the two flow paths (a first flow path and a second flow path). The liquid discharge tube 4b is individually formed for these flow paths 4c. Hence, the amount of sensing object adsorbed in the adsorption layer 14 is increased as compared with the example described previously, with the result that it is possible to obtain the sensing device having a higher sensitivity. In FIG. 16, the adsorption layer 14 is omitted.

Here, when the dedicated flow paths 4c are formed for the arm portions 13a and 13b, the sample solution preferentially flows through, among these two flow paths 4c, the flow path 4c through which the sample solution flows more easily (which has a low resistance). In other words, even if the surface tensions of these flow paths 4c and 4c attempt to be made equal to each other, and the smoothness of the surface of the common electrode 11, the hydrophilicity of the adsorption layer 14 and the like are significantly low, a difference between the flow paths 4c and 4c occurs. The sample solution itself flows, based on such a difference, one of the two flow paths 4c and 4c.

Figure 17:
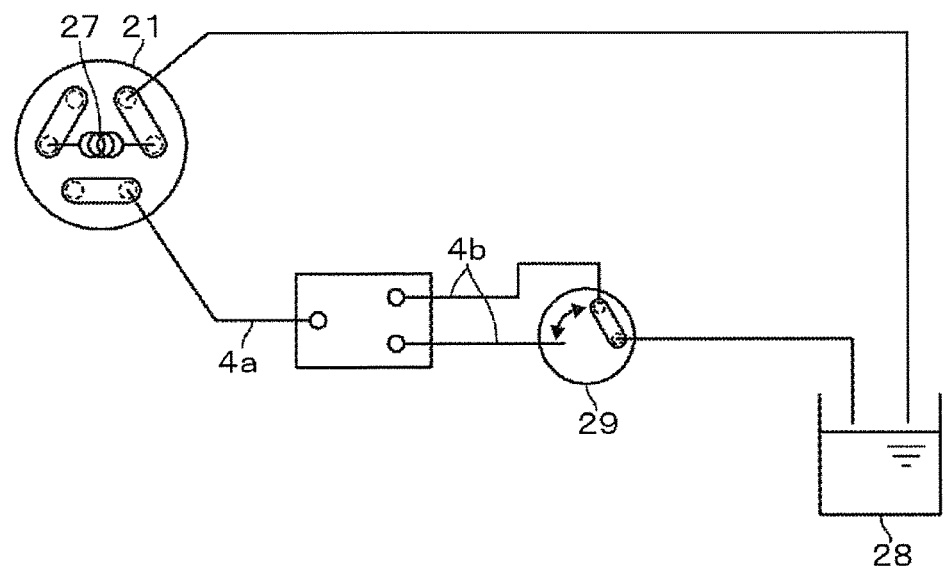
FIG. 17 is a schematic view showing the part of the sensing device in the another example.
Figure 18:
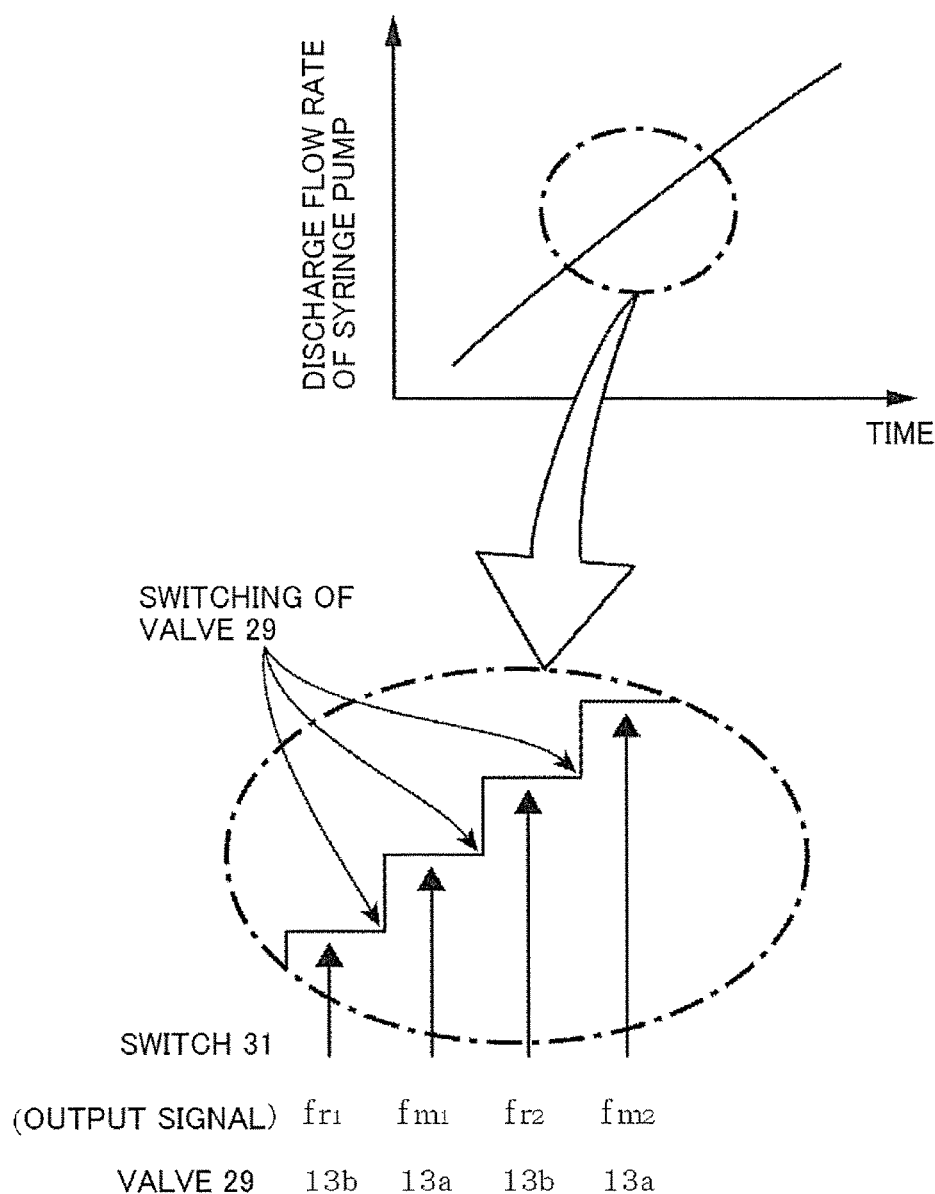
FIG. 18 is a schematic view schematically showing an action of the sensing device in the another example.

Hence, in this example, in order to pass the liquid uniformly through the two flow paths 4c and 4c, as shown in FIG. 17, on the downstream side of the sensor unit 1, a discharge switching valve 29 for switching the two liquid discharge tubes 4b and 4b is provided to alternately switch these flow paths 4c and 4c. As described previously, while the switch portion 31 is being switched at a high speed, this discharge switching valve 29 is also switched.

As described above, when the discharge switching valve 29 is switched, it is preferable to reduce variations in the discharge pressure of the liquid supplied to the arm portions 13a and 13b. Specifically, although the buffer solution holding portion 24 described previously discharges the buffer solution at a constant speed, when seen microscopically as an enlarged part is shown in the lower side of FIG. 18, the forward movement of the liquid pressing portion 24b (syringe) is intermittently repeated.

Hence, when in this example, the sensing object is detected, in order for variations in the pressure of the liquid between the arm portions 13a and 13b to be reduced, while the liquid pressing portion 24b is stopped, the switch portion 31 is switched, and the oscillation frequency is measured. Moreover, in order for the flow rates of the sample solution flowing through the surface of the crystal unit 2 to be made equal to each other in the arm portions 13a and 13b, the timing at which the liquid pressing portion 24b is moved forward and the timing at which the discharge switching valve 29 is switched are synchronized. Specifically, when the liquid pressing portion 24b starts the forward movement from the state where the forward movement is stopped, the discharge switching valve 29 is switched. Thus, it is possible to reduce variations in the discharge pressure of the sample solution while the sensing object is adsorbed to each of the adsorption layers 14 as much as possible. In the example as described above, since a variation in stress caused when the discharge switching valve 29 is switched is likely to become noise to produce adverse effects, for the measurement of the oscillation frequency, the movement average of chronological data on the oscillation frequency may be used.

The discharge switching valve 29 described above may be provided on the upstream side with respect to the sensor unit 1 instead of being provided on the downstream side of the sensor unit 1.

Figure 19:
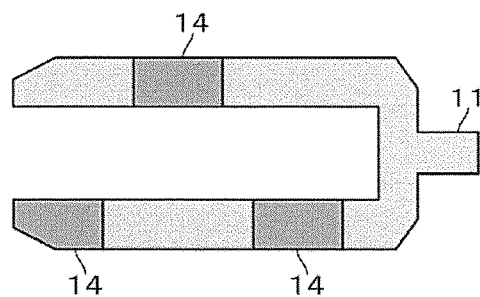
FIG. 19 is a plan view showing another example of the sensing device.

Although in the example described above, the pair of the adsorption region 14a (14b) and the reference region 16a (16b) is arranged in two places in the direction of the flow of the liquid, as shown in FIG. 19, it may be formed in three places. The pair described above may be provided in four places or more in the direction of the flow of the liquid.

Although the oscillation circuit 32 is provided in common in the regions 14a, 14b, 16a and 16b, it may be provided in each of the regions 14a, 14b, 16a and 16b. Furthermore, the fluid containing the sensing object may be a sample gas instead of the sample solution. In this case, as the sensing object contained in the sample gas, for example, dioxin is detected.

What is claimed is:

1. A sensing device that passes, on one surface side of a piezoelectric piece, a fluid containing a sensing object from a front side to a rear side and that makes an adsorption layer on a surface of a common electrode formed on the one surface side of the piezoelectric piece adsorb the sensing object to sense the sensing object, the sensing device comprising:

the common electrode containing a first electrode portion and a second electrode portion which are separated from each other in a left and right direction, and each of said first and second electrode portions extends along a front and rear direction, the first electrode portion and the second electrode portion being connected to a common ground electrode;

the first electrode portion being sectioned to a first adsorption region located in the front side and a reference region located in the rear side, a first adsorption layer being formed on a surface of the first electrode portion in the first adsorption region, an adsorption layer being not formed on a surface of the first electrode portion in the reference region, the second electrode portion being sectioned to a reference region located in the front side and a second adsorption region located in the rear side, the second adsorption layer being formed on a surface of the second electrode portion in the second adsorption region, an adsorption layer being not formed on a surface of the second electrode portion in the reference region located in the front side;

when the reference region of the second electrode portion is referred to as a first reference region, and the reference region of the first electrode portion is referred to as a second reference region, first opposite electrodes which are individually formed on the other surface side of the piezoelectric piece so as to be opposite the first adsorption region and the first reference region, respectively;

second opposite electrodes which are individually formed on the other surface side of the piezoelectric piece so as to be opposite the second adsorption region and the second reference region, respectively;

a flow path formation member for passing, on the one surface side of the piezoelectric piece, the fluid containing the sensing object from the front side to the rear side;

an oscillation circuit for oscillating the piezoelectric piece;

a frequency measurement portion for measuring an oscillation frequency of the oscillation circuit; and a control portion for determining:
  a first difference between an oscillation frequency of the piezoelectric piece between the first adsorption region and the first opposite electrode and an oscillation frequency of the piezoelectric piece between the first reference region and the first opposite electrode, and
  a second difference between an oscillation frequency of the piezoelectric piece between the second adsorption region and the second opposite electrode and an oscillation frequency of the piezoelectric piece between the second reference region and the second opposite electrode, so as to calculate a sum value of the first difference and the second difference.

2. The sensing device according to claim 1, wherein
when a dimension of the first adsorption region in the direction intersecting the direction of the flow of the fluid is W1, a dimension of the second adsorption region in the direction intersecting the direction of the flow of the fluid is W2 and a width dimension of the flow path formed by the flow path formation member in the direction intersecting the direction of the flow of the fluid is L, (W1+W2)/L>0.5.

3. The sensing device according to claim 1, wherein
the oscillation circuit includes:
  a first oscillation circuit that oscillates a first sensor portion which includes the first adsorption region and the first reference region; and
  a second oscillation circuit that oscillates a second sensor portion which includes the second adsorption region and the second reference region.

4. The sensing device according to claim 1, wherein
the flow path formation member further includes: a fluid supply port,
on an upstream side of the fluid supply port, a liquid pressing portion that switches inflow of the fluid from the fluid supply port and stop of the inflow of the fluid, and
a switch portion that switches a region of the piezoelectric piece connected to the oscillation circuit between a first sensor portion which includes the first adsorption region and the first reference region and a second sensor portion which includes the second adsorption region and the second reference region are provided, and
the control portion performs control so as to switch the switch portion between the first sensor portion and the second sensor portion when the inflow of the fluid from the fluid supply port is stopped, such that the oscillation frequency is measured.

5. The sensing device according to claim 4, wherein
the control portion performs control so as to switch the switching portion between a first flow path and a second flow path, when the liquid pressing portion switches from the stop of the inflow of the fluid to the inflow of the fluid,
wherein the first flow path along which the fluid passes through the rust adsorption region and the second reference region,
the second flow path along which the fluid passes through the first reference region and the second adsorption region.

* * * * *